United States Patent [19]

Reimer

[11] 4,336,110

[45] Jun. 22, 1982

[54] SEPARATION OF BENZENE FROM CYCLOHEXANE

[75] Inventor: Ronald A. Reimer, Orange, Tex.

[73] Assignee: E. I. Du Pont de Nemours and Company, Wilmington, Del.

[21] Appl. No.: 231,794

[22] Filed: Feb. 5, 1981

[51] Int. Cl.³ .......................... B01D 3/40; C07C 7/08
[52] U.S. Cl. ..................................... 203/60; 585/860; 585/864
[58] Field of Search ............... 203/60, 57; 208/313, 208/330; 585/860, 864

[56] References Cited

U.S. PATENT DOCUMENTS

| | | | |
|---|---|---|---|
| 2,279,194 | 4/1942 | Field | 203/60 |
| 2,441,827 | 5/1948 | McKinnis | 203/60 |
| 2,763,604 | 9/1956 | Dorsey et al. | 203/60 |
| 2,842,484 | 7/1958 | Fleck | 585/860 |
| 3,725,207 | 4/1973 | Golden | 203/60 |
| 4,168,209 | 9/1979 | Mikitenko et al. | 203/60 |

FOREIGN PATENT DOCUMENTS 585850  2/1947  United Kingdom ............. 585/860

Primary Examiner—Wilbur L. Bascomb, Jr.

[57] ABSTRACT

Separation of benzene from cyclohexane by distillation in the presence of selected nitriles.

3 Claims, 1 Drawing Figure

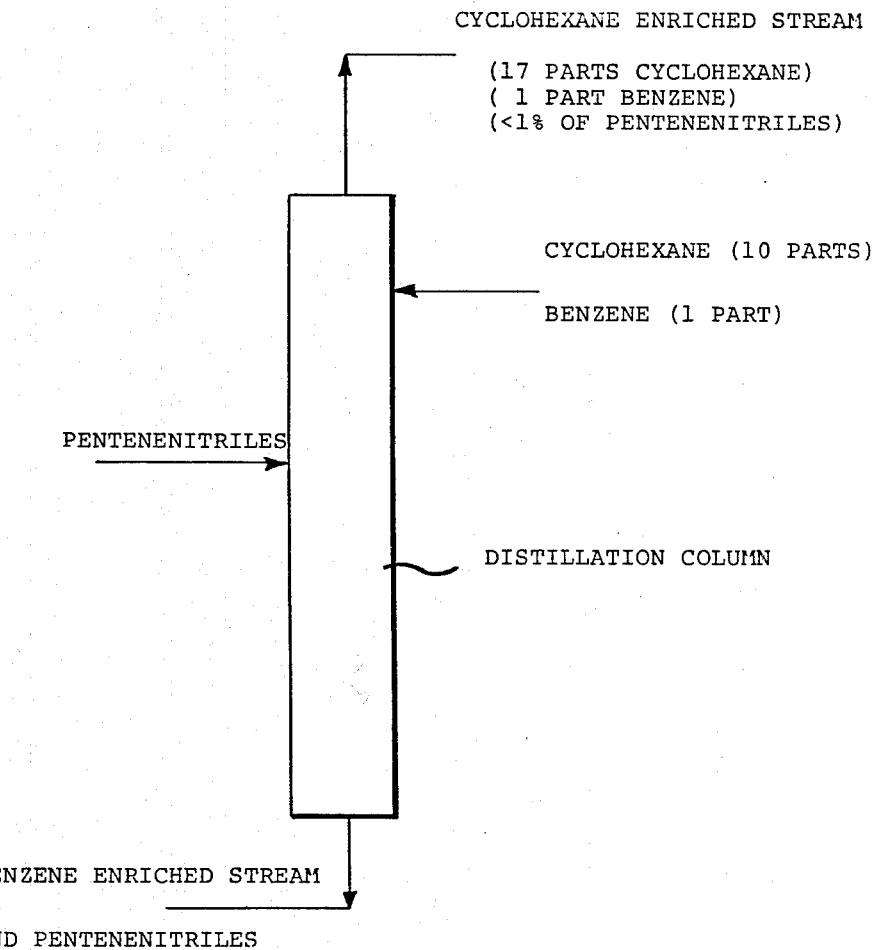

> 4,336,110

SEPARATION OF BENZENE FROM CYCLOHEXANE

BACKGROUND OF THE INVENTION

1. Field of the Invention

The present invention relates to the separation of benzene and cyclohexane and, more particularly, to the use of distillation in the presence of selected nitriles to obtain a stream enriched in benzene relative to the initial stream as the tails from the distillation and a stream enriched in cyclohexane relative to the initial stream as the heads from the distillation.

2. Description of the Prior Art

Numerous processes have been suggested for separating hydrocarbons having similar boiling points including chemical processes, highly efficient fractional distillation, azeotropic distillation and solvent extraction both in the liquid and vapor phase, *Technique of Organic Chemistry*, IV, "Distillation" Rose et al, Interscience Publishers, Inc. N.Y. (1951). Glycols and sulfolanes are the most common solvents although methylglutaronitrile is alleged to be extremely efficient, "Refining Petroleum for Chemicals" ACS Monograph No. 97, Chap. 15, 1971.

U.S. Pat. No. 2,441,827 issued on May 18, 1948 discloses a process for the separation of relatively olefinic hydrocarbons from relatively nonolefinic hydrocarbons which employs a large class of nitriles to selectively dissolve at least one of the hydrocarbons of the hydrocarbon mixture without dissolving substantial quantities of the other hydrocarbon or hydrocarbons in the mixture. The patentee discloses that the extraction process may be conducted in a liquid phase by thoroughly mixing an appropriate amount of the nitrile with the hydrocarbon mixture, allowing the mixture to separate into two liquid phases and separating the two phases by decantation. An alternate method for practicing the process is to effect the solvent extraction in the vapor phase by contacting the mixture of hydrocarbons in a fractionating column with the liquid solvent to permit scrubbing of the vapors by the solvent whereupon the soluble hydrocarbon is removed from the vapor phase by the solvent and passes downwardly to the base of the column. The Patentee discloses that if it is desired to vaporize the mixture, the solvent should condense before the hydrocarbon so that the liquid solvent can then contact the hydrocarbon vapors and solubilize at least one of the components.

SUMMARY OF THE INVENTION

A method for reducing the benzene content in an initial stream comprising, or consisting essentially of, benzene and cyclohexane which comprises subjecting said stream to distillation in the presence of at least one unsaturated nitrile having 4 to 6 carbon atoms and thereafter recovering a stream enriched in cyclohexane relative to said initial stream as an overhead distillate and a stream enriched in benzene relative to said initial stream as the tails from the distillation.

Pentenenitriles are preferred.

DETAILED DESCRIPTION OF THE INVENTION

The method of the present invention may be applied to any stream which comprises, or consists essentially of, benzene and cyclohexane or compounds whose structures closely resemble benzene and cyclohexane. The mole ratio of benzene to cyclohexane can vary over a wide range but usually is in the range of 1/95 to 15/1 and is particularly advantageous at a molar ratio of benzene to cyclohexane in the range of 1/30 to 1/1.

The nitriles which are operable in the present invention are those unsaturated nitriles having 4 to 6 carbon atoms in the main chain, e.g., butenenitriles, pentenenitriles and hexenenitriles. The preferred nitriles are those having 5 carbon atoms including nitriles having 4 carbon atoms in the main chain and a methyl group in the second or third position with a double bond in the second or third position e.g., 2 methyl-3-butenenitrile and, most preferably, cis- and trans- pentenenitriles, for example, 3-pentenenitrile and 4-pentenenitrile, or mixtures of nitriles wherein the pentenenitriles are the major components. The amount of nitrile employed in the present method should be at least about 20% but usually not more than 90% by weight based upon the combined weight of the benzene and cyclohexane. About 80% to 95% is preferred. Minor amounts of nitriles other than those set forth hereinabove may also be present provided that these other nitriles do not cause the formation of a multiple liquid phase system.

The apparatus employed to accomplish the present distillation is believed obvious to one skilled in the art. Essentially any type of batch or continuous distillation column can be employed but generally it is desirable in a benzene-cyclohexane system to employ a column havng 10 to 30 actual plates and to operate the column at a head pressure of 0.5 to 2 atm and a head temperature of 60° to 110° C.

The present invention is particularly advantageous in a system wherein the nitriles, e.g., pentenenitrile are already present as a stream from another portion of the process such as the process described in "Hexamethylene Diamine", *Process Economics Program Report No. 31-A*, Stanford Research Institute, Menlo Park, CA, (1972). The present invention is particularly advantageous when the hydrocyanation employs an arylborane as a catalyst promoter, see U.S. Pat. No. 3,798,256, and the benzene from the decomposition of the arylborane must be purged.

The nitriles employed in the present invention avoid the formation of a multiple liquid phase and therefore phase separation is not required. The nitriles of the present invention do not preferentially dissolve either the benzene or the cyclohexane but effect the separation by preferentially elevating the boiling point of benzene relative to cyclohexane.

The following examples are presented to illustrate but not to restrict the present invention. Parts and percentages are by weight unless otherwise specified.

EXAMPLE I

Approximately 1,056 parts of a mixture of 5 carbon unsaturated nitriles (predominately trans-3-pentenenitrile) and containing less than 4% by weight of saturated nitrile along with 396 parts of cyclohexane and 628 parts of benzene were charged to the pot of a 30 plate Oldershaw column. Reflux was established at 700 mmHg and the contents of the pot were heated for 3 hours during which time 957 parts of make was removed at a reflux ratio of 5/1. During the distillation the head temperature of the column increased from 73° to 85° C. and the pot temperature increased from 90° C. to 135° C. At the end of the 3 hour period samples of the overhead and pot were removed and analyzed. The results are summarized in Table I.

TABLE I

| | Initial | After Distillation | |
|---|---|---|---|
| | Charge | Tails | Heads |
| Compound | % | % | % |
| Cyclohexane | 19.1 | 0.019 | 41.5 |
| Benzene | 30.3 | 4.0 | 57.2 |

The above results indicate that substantially more benzene remained in the tails relative to cyclohexane. In the absence of the pentenenitriles substantially no separation is noted

EXAMPLE II

Varying amounts of the mixture of pentenenitriles similar to Example I, benzene and cyclohexane were charged to the pot of an Othmer still and the contents refluxed at atmospheric pressure until the vapor temperature remained constant for one hour. Samples of the liquid and condensed vapor were then removed and analyzed. The results are presented in Table II.

TABLE II

| Vapor Temperature (°C.) | Liquid Composition (%) | | | Vapor Composition (%) | | |
|---|---|---|---|---|---|---|
| | Pentenenitriles | Benzene | Cyclohexane | Pentenenitriles | Benzene | Cyclohexane |
| 122 | 90.6 | 5.08 | 3.06 | 47.0 | 21.8 | 32.5 |
| 104 | 78.4 | 12.0 | 8.72 | 21.6 | 27.5 | 49.0 |
| 88 | 53.4 | 24.9 | 21.9 | 9.9 | 36.3 | 56.6 |
| 81 | 27.5 | 39.1 | 34.6 | 3.84 | 42.7 | 56.0 |
| 79 | 13.6 | 45.9 | 42.4 | 2.51 | 47.0 | 53.0 |
| 86 | 52.4 | 5.4 | 40.3 | 7.9 | 6.9 | 87.1 |
| 86 | 55.0 | 14.8 | 30.8 | 7.5 | 20.0 | 74.8 |
| 90 | 53.9 | 33.8 | 11.4 | 6.9 | 51.7 | 39.4 |
| 93 | 52.2 | 43.0 | 3.28 | 8.5 | 80.0 | 12.8 |
| 77* | — | 51.5 | 49.3 | — | 51.4 | 49.5 |

*(Control)

Except for the control which contained no pentenenitriles, at all reported concentrations the vapor was enriched in cyclohexane (relative to benzene) as compared to the liquid.

In continuous operation a standard distillation column of at least about 20 actual plates having a reflux system can be employed. A stream containing 20–50% benzene and cyclohexane with balance being 5 carbon nitriles at a weight ratio of cyclohexane to benzene of about 10/1 is introduced near the top plate of the column and a stream containing predominately pentenenitriles at a weight ratio of nitriles to total benzene and cyclohexane of about 75/1 is introduced near the midpoint of the column. After establishing boiling at atmospheric pressure and at a reflux ratio of about 0.8, continuous feed and drawoff are established. The weight ratio of cyclohexane to benzene in the overhead drawoff is about 17/1 with less than 1% of the nitriles in the overhead drawoff with the remaining cyclohexane benzene and nitriles removed as tails. All liquid products are single phase.

I claim:
1. A method for reducing the benzene content in an initial stream comprising benzene and cyclohexane which comprises subjecting said stream to distillation in the presence of at least one unsaturated nitrile having 4–6 carbon atoms and recovering a stream enriched in cyclohexane relative to said initial stream as an overhead distillate and a stream enriched in benzene relative to said initial stream as the tails from the distillation in a single liquid phase.
2. The method of claim 1 wherein said nitriles consist essentially of pentenenitriles.
3. The method of claims 1 and 2 wherein the weight ratio of nitriles to the total weight of benzene and cyclohexane introduced is at least 2/1.

* * * * *